US011001557B2

(12) United States Patent
Baba et al.

(10) Patent No.: US 11,001,557 B2
(45) Date of Patent: May 11, 2021

(54) ANTIVIRAL DRUG FOR SEVERE FEVER WITH THROMBOCYTOPENIA SYNDROME

(71) Applicants: Kagoshima University, Kagoshima (JP); Nobelpharma Co., Ltd., Tokyo (JP)

(72) Inventors: Masanori Baba, Kagoshima (JP); Masaaki Toyama, Kagoshima (JP); Norikazu Sakakibara, Kagawa (JP)

(73) Assignees: Kagoshima University, Kagoshima (JP); Nobelpharma Co., Ltd., Tokyo (JP)

( * ) Notice: Subject to any disclaimer, the term of this patent is extended or adjusted under 35 U.S.C. 154(b) by 0 days.

(21) Appl. No.: 16/479,081

(22) PCT Filed: Jan. 16, 2018

(86) PCT No.: PCT/JP2018/000887

§ 371 (c)(1),
(2) Date: Jul. 18, 2019

(87) PCT Pub. No.: WO2018/135449

PCT Pub. Date: Jul. 26, 2018

(65) Prior Publication Data

US 2019/0389803 A1 Dec. 26, 2019

(30) Foreign Application Priority Data

Jan. 19, 2017 (JP) ............................ JP2017-007507

(51) Int. Cl.

| | |
|---|---|
| *C07D 215/44* | (2006.01) |
| *A61P 31/12* | (2006.01) |
| *C07D 401/12* | (2006.01) |
| *C07D 413/12* | (2006.01) |
| *C07D 417/12* | (2006.01) |

(52) U.S. Cl.
CPC ............ *C07D 215/44* (2013.01); *A61P 31/12* (2018.01); *C07D 401/12* (2013.01); *C07D 413/12* (2013.01); *C07D 417/12* (2013.01)

(58) Field of Classification Search
CPC ................ A61K 31/47; A61K 31/4706; A61K 31/4709; C07D 215/38; C07D 215/44; C07D 401/12; A61P 31/12
See application file for complete search history.

(56) References Cited

U.S. PATENT DOCUMENTS

| | | | |
|---|---|---|---|
| 2004/0152729 A1 | 8/2004 | Park et al. | |
| 2009/0226401 A1 | 9/2009 | Kim et al. | |
| 2020/0113891 A1* | 4/2020 | Davey | A61P 31/14 |

FOREIGN PATENT DOCUMENTS

| | | |
|---|---|---|
| JP | 2009-527478 A | 7/2009 |
| WO | 2018191642 A1 | 10/2018 |

OTHER PUBLICATIONS

Heindel, J Med Chem, 1970, vol. 13(1), 156-157. (Year: 1970).*
Warhurst, Ann Trop Med Parasitol, vol. 76(3), 257-264, 1982. (Year: 1982).*
Conroy, J Med Chem, vol. 71, 1949, 3236-3237. (Year: 1949).*
Baba, Masanori; et al., "Establishment of an antiviral assay system and identification of severe fever with thrombocytopenia syndrome virus inhibitors", Antivir. Chem. Chemother., 2017, vol. 25, No. 3, pp. 83-89.
Extended European Search Report for Corresponding European Application No. 18741625.0, dated Sep. 9, 2020, 7 pages.

* cited by examiner

*Primary Examiner* — D Margaret M Seaman
(74) *Attorney, Agent, or Firm* — Lucas & Mercanti, LLP

(57) ABSTRACT

The present invention pertains to an antiviral drug for severe fever with thrombocytopenia syndrome, which contains a compound represented by formula (I) or a salt thereof, or a solvate of the compound or salt (In the formula, R1 and R2 are the same or different from each other, and each represents a substituted or unsubstituted C1-10 alkyl group, R1 and R2 may form a substituted or unsubstituted 5- or 6-member ring in conjunction with an adjacent nitrogen atom, and X represent a halogen atom.)

9 Claims, 5 Drawing Sheets

| Lane No. | Sample | Treatment method |
|---|---|---|
| 1 | Patient no.1 (5/17 onset) 5/24 sampling | RNA extraction |
| 2 | 〃 | Lysis Buffer treatment |
| 3 | Patient no.2 (3/26 onset) 4/04 sampling | RNA extraction |
| 4 | 〃 | Lysis Buffer treatment |
| 5 | Patient no.1-serum inoculation, Vero cell supernatant | RNA extraction |
| 6 | 〃 | Lysis Buffer treatment |
| 7 | Patient no.2-serum inoculation, Vero cell supernatant | RNA extraction |
| 8 | 〃 | Lysis Buffer treatment |

| Drug | $EC_{50}$ (μM) | $CC_{50}$ (μM) |
|---|---|---|
| Ribavirin | 40.1 ± 16.3 | > 100 |
| Favipiravir | 25.0 ± 9.3 | > 100 |
| Amodiaquine | 19.1 ± 5.1 | > 100 |

Data: mean values and sd values of three experiments

A: Amodiaquine, F: Favipiravir, R: Ribavirin, L: Lamivudine

ANTIVIRAL DRUG FOR SEVERE FEVER WITH THROMBOCYTOPENIA SYNDROME

CROSS-REFERENCE TO RELATED APPLICATIONS

This application is a 371 of PCT/JP2018/000887, filed Jan. 16, 2018, which claims benefit of Japanese Patent Application No. 2017-007507, filed on Jan. 19, 2017.

TECHNICAL FIELD

The present invention relates to an antiviral drug for severe fever with thrombocytopenia syndrome.

BACKGROUND ART

Severe fever with thrombocytopenia syndrome (SFTS) is a tick-borne infection caused by severe fever with thrombocytopenia syndrome virus (SFTSV), which is newly found and classified in the genus *Phlebovirus* belonging to the family Bunyaviridae, as reported by Chinese researchers in 2011. In this country, SFTS was first reported in 2013 and is an infection with an extremely high mortality rate. Currently, 226 patients (as of Nov. 30, 2016) are reported mainly in the west of Japan, and 52 patients of them are dead.

Amodiaquine has been already approved as an antimalarial drug for clinical use. A 7-chloro-4-aminoquinoline compound such as amodiaquine is known to be effective for Parkinson's disease. However, the relationship between 7-chloro-4-aminoquinoline compound such as amodiaquine and anti-SFTSV activity has not yet been reported, up to present.

CITATION LIST

Patent Literature

Patent Literature 1: JP Patent Publication (Kohyo) 2009-527478 A

SUMMARY OF INVENTION

Problem to be Solved

An object of the present invention is to provide an antiviral drug effective for SFTSV.

Means for Solving Problem

The present inventors, with a view to attaining the object, separated SFTSV from the blood of patients with SFTS and established an antiviral assay system using the SFTSV. Using the assay system, for examining an antiviral activity, we further conducted an anti-SFTSV activity test for various drugs. As a result, we successfully found anti-SFTSV activity, which is selective for amodiaquine which is presently approved as an antimalarial drug for clinical use and a predetermined derivative(s) of them. Based on the finding, the present invention was accomplished.

More specifically, the present invention will be summarized as follows.

(1) An antiviral drug for severe fever with thrombocytopenia syndrome, comprising a compound represented by the following formula (I):

[Formula 1]

(I)

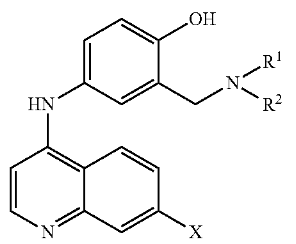

wherein $R^1$ and $R^2$, which are the same or different, each represent a substituted or unsubstituted $C_{1-10}$-alkyl group and may join with an adjacent nitrogen atom to form a substituted or unsubstituted 5-membered ring or 6-membered ring; and X represents a halogen atom, or a salt thereof or a solvate thereof.

(2) The antiviral drug for severe fever with thrombocytopenia syndrome according to (1), wherein, in the formula (I), $R^1$ and $R^2$, which are the same or different, each represent a substituted or unsubstituted $C_{1-6}$-alkyl group and may join with an adjacent nitrogen atom to form a substituted or unsubstituted 5-membered ring or 6-membered ring; and X represents a halogen atom.

(3) The antiviral drug for severe fever with thrombocytopenia syndrome according to (1) or (2), for use in prevention or treatment of severe fever with thrombocytopenia syndrome.

(4) A compound represented by the following formula (Ia):

[Formula 2]

(Ia)

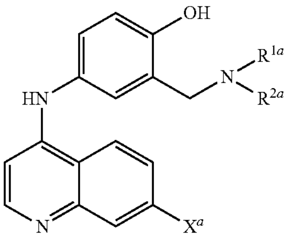

wherein $R^{1a}$ and $R^{2a}$ represent a combination of a methyl group and a $C_{1-10}$-alkyl group, a combination of an ethyl group and a $C_{3-10}$-alkyl group, or a combination of an ethyl group and a 2-hydroxyethyl group, and may join with an adjacent nitrogen atom to form a substituted or unsubstituted 5-membered ring or 6-membered ring; $X^a$ represents an iodine atom or a fluorine atom; if $X^a$ represents a fluorine atom, $R^{1a}$ and $R^{2a}$ may be an ethyl group and an ethyl group, or a salt thereof or a solvate thereof.

Effects of the Invention

According to the present invention, it is possible to provide an antiviral drug effective for SFTSV.

DESCRIPTION OF EMBODIMENTS

Figure 1:
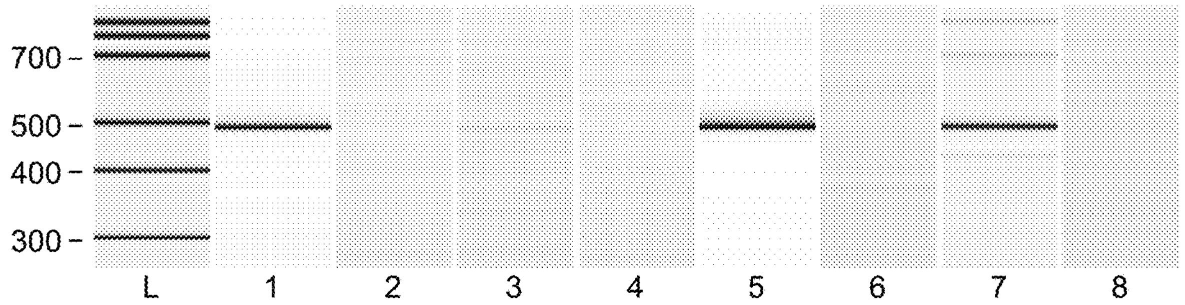
FIG. 1 shows the results of electrophoresis when the gene of SFTSV was identified from a patient's specimen directly or a culture of cells inoculated with a patient's specimen.

Now, the present invention will be described below in detail.

Examples of the $C_{1-10}$-alkyl group represented by $R^1$ or $R^2$ in the formula (I) include, a methyl group, an ethyl group, a propyl group, an isopropyl group, a butyl group, an isobutyl group, a sec-butyl group, a tert-butyl group, a pentyl group, an isopentyl group, a hexyl group, a heptyl group, an octyl group, a nonyl group, a decyl group, a cyclopropyl group, a cyclobutyl group, a cyclopentyl group and a cyclohexyl group. Examples of the $C_{1-6}$-alkyl group represented by $R^1$ or $R^2$ in the formula (I) include a methyl group, an ethyl group, a propyl group, an isopropyl group, a butyl group, an isobutyl group, a sec-butyl group, a tert-butyl group, a pentyl group, an isopentyl group, a hexyl group, a cyclopropyl group, a cyclobutyl group, a cyclopentyl group and a cyclohexyl group.

The said $C_{1-10}$-alkyl group and said $C_{1-6}$-alkyl group may be substituted with one or more substituents selected from, for example, a $C_{1-6}$-alkoxy group such as a methoxy group, an ethoxy group, a propoxy group, an isopropoxy group, a butoxy group, an isobutoxy group, a sec-butoxy group, a tert-butoxy group, a pentyloxy group, an isopentyloxy group, a hexyloxy group, a cyclopropyloxy group, a cyclobutyloxy group, a cyclopentyloxy group and a cyclohexyloxy group; a $C_{1-6}$-alkoxy-carbonyl group such as a methoxy carbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentyloxycarbonyl group, an isopentyloxy carbonyl group, a cyclopropyloxycarbonyl group, a cyclobutyloxycarbonyl group and a cyclopentyloxycarbonyl group; a hydroxyl group; an aromatic hydrocarbon group such as a phenyl group, a tolyl group and a naphthyl group; a halogen atom such as a fluorine atom, a chlorine atom, a bromine atom and an iodine atom; a $C_{1-6}$-aliphatic acyl group such as a formyl group, an acetyl group, a propionyl group (propanoyl group), a butyryl group (butanoyl group), a valeryl group (pentanoyl group) and a hexanoyl group; an aromatic acyl group (aroyl group) such as a benzoyl group, a toluoyl group; an aralkyloxy group, a carboxyl group, an amino group, a $C_{1-6}$-alkylamino group and a di-$C_{1-6}$-alkylamino group.

Examples of the 5-membered ring group or 6-membered ring group formed by joining $R^1$ and $R^2$ or $R^{1a}$ and $R^{2a}$ with an adjacent nitrogen atom include a 1-pyrrolidinyl group, a 1-imidazolidinyl group, a 1-pyrazolidinyl group, a morpholino group (4-morpholinyl group), a piperidino group (1-piperidinyl group), a 1-piperazinyl group and a 4-thiamorpholinyl group. These 5-membered ring groups and 6-membered ring groups may be substituted with one or more substituents selected from a $C_{1-6}$-alkyl group, a $C_{2-6}$-alkenyl group, a $C_{2-6}$-alkynyl group, an aromatic group, an acyl group, a hydroxyl group, a carboxyl group, a cyano group, a halogen atom, a $C_{1-6}$-alkoxy group, an aralkyl group, a nitro group, an amino group, a $C_{1-6}$-alkylamino group, a di-$C_{1-6}$-alkylamino group, and the like. Examples of the 5-membered ring group or 6-membered ring group preferably include a substituted or unsubstituted 1-pyrrolidinyl group, a substituted or unsubstituted 1-piperidinyl group, a substituted or unsubstituted morpholino group (4-morpholinyl group), a substituted or unsubstituted 4-thiamorpholinyl group and a substituted or unsubstituted piperidino group (1-piperidinyl group).

Examples of a halogen atom represented by X in the formula (I) include a fluorine atom, a chlorine atom, a bromine atom, and an iodine atom.

Of the compounds represented by the formula (I), the compounds represented by the formula (Ia), for example, a compound of No. 2 shown in the following Table 1 and compounds of Nos. 7 to 22 described in Example 8 are novel compounds.

Of the compounds represented by the formula (I), compounds wherein the total number of carbon atoms of $R^1$ and $R^2$ is 4 or more, for example, a compound wherein $R^1$ and $R^2$ represent a combination of a methyl group and a $C_{3-10}$-alkyl group or a combination of an ethyl group and a $C_{2-10}$-alkyl group; or a compound wherein $R^1$ and $R^2$ join with an adjacent nitrogen atom to form a substituted or unsubstituted 5-membered ring or 6-membered ring and X represents a chlorine atom or an iodine atom is preferable and a compound wherein $R^1$ is a methyl group and $R^2$ is a $C_{4-6}$-alkyl group, is further preferable.

Of the compounds represented by the formula (I), amodiaquine and the compound of No. 5 shown in the following Table 1 are commercially available. The commercially available compounds can be directly or, after purified, if necessary, used as an active ingredient in the present invention.

The salt of a compound represented by the formula (I) is preferably a pharmaceutically acceptable salt, and examples of the salt include a salt of the compound with an inorganic acid such as hydrochloric acid, sulfuric acid, phosphoric acid, hydrobromic acid, hydroiodic acid, nitric acid, pyrosulfuric acid and metaphosphoric acid or with an organic acid such as citric acid, benzoic acid, acetic acid, propionic acid, fumaric acid, maleic acid and sulfonic acid (for example, methanesulfonic acid, p-toluene sulfonic acid, naphthalene sulfonic acid).

Examples of a solvate of a compound represented by the formula (I) or a salt thereof include a hydrate.

A compound represented by the formula (I) can be produced by a method known in the art, for example, as follows.

[Formula 3]

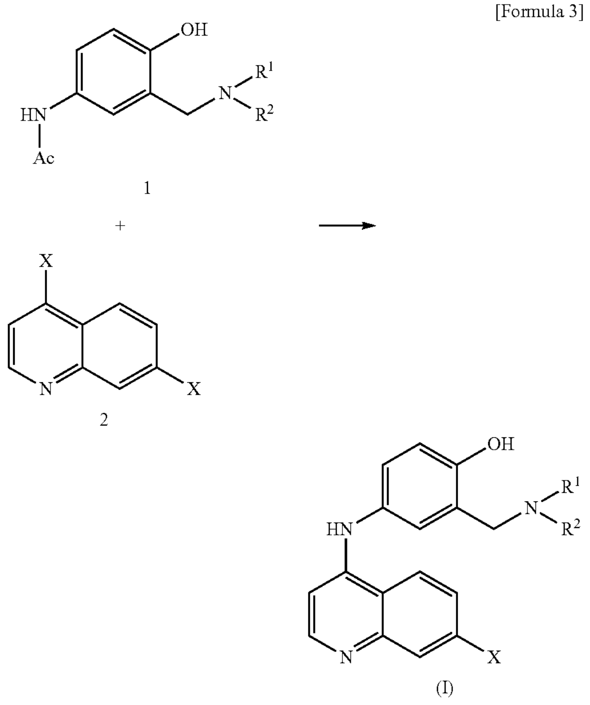

wherein $R^1$, $R^2$ and X are the same as defined above and Ac represents an acetyl group.

More specifically, 4-acetamido-2-(N,N-disubstituted aminomethyl)phenol (1) is heated in ethanol/hydrochloric acid and hydrolyzed. Then, a hydrolyzed product is reacted with 4,7-dihaloquinoline (2). In this manner, a desired compound (I) can be produced.

The product obtained as mentioned above may be purified by a customary method, for example, column chromatography using, e.g., silica gel, as a carrier and a recrystallization method using, e.g., methanol, ethanol, chloroform, dimethyl sulfoxide, n-hexane-ethyl acetate or water. Examples of an elution solvent for column chromatography include methanol, ethanol, chloroform, acetone, hexane, dichloromethane, ethyl acetate and mixed solvents of these.

The compound as mentioned above can be used as an anti-SFTSV drug in combination with a customary pharmaceutical carrier. The dosage form thereof is not particularly limited and appropriately selected and used depending on needs. Examples of the dosage form include oral agents such as a tablet, a capsule, a granule, a fine granule, a powder, a sustained release preparation, a liquid preparation, a suspension, an emulsion, a syrup and an elixir and parenteral agents such as an injection and a suppository.

An oral agent is produced by using, for example, starch, lactose, sucrose, mannitol, carboxymethylcellulose and inorganic salts in accordance with an ordinary method. In addition to these components, e.g., a binder, a disintegrant, a surfactant, a lubricant, a glidant, a flavoring agent, a colorant and/or a perfume can be appropriately added.

Examples of the binder include starch, dextrin, gum Arabic, gelatin, hydroxypropyl starch, methylcellulose, sodium carboxymethylcellulose, hydroxypropylcellulose, crystalline cellulose, ethyl cellulose, polyvinyl pyrrolidone and macrogol.

Examples of the disintegrant include starch, hydroxypropyl starch, sodium carboxymethylcellulose, calcium carboxymethylcellulose, carboxymethylcellulose and a low-substituted hydroxypropylcellulose.

Examples of the surfactant include sodium lauryl sulfate, soy lecithin, sucrose fatty acid ester and polysorbate 80.

Examples of the lubricant include talc, wax, hydrogenated vegetable oil, sucrose fatty acid ester, magnesium stearate, calcium stearate, aluminum stearate and polyethylene glycol.

Examples of the glidant include light anhydrous silicic acid, dry aluminum hydroxide gel, synthetic aluminum silicate and magnesium silicate.

An injection is produced in accordance with an ordinary method. As a diluent, generally, distilled water for injection, saline, a glucose solution, olive oil, sesame oil, peanut oil, soybean oil, corn oil, propylene glycol, polyethylene glycol, and/or the like can be used. If necessary, a disinfectant, a preservative, a stabilizer, an isotonic agent, a soothing agent, and/or the like may be added. In view of stability, an injection can be added in, e.g., a vial, frozen and subjected to ordinary lyophilization to remove a water content. From the lyophilized injection, a liquid preparation can be prepared again immediately before use. The content of a compound of the formula (I) in the injection may be varied between the 5 and 50 wt %; however, the content is not limited to this.

Examples of other parenteral agents include a suppository for intrarectal administration. The suppository can be produced in accordance with an ordinary method.

The administration schedule of an anti-SFTSV drug formulated varies depending on, e.g., the dosage form and the route of administration, and, for example, can be administered once to four times per day in a period from a week to 3 months.

In order to obtain a desired effect, the dose of an oral agent, which varies depending on the age, body weight and severity of a disease of a patient, is usually, for example, 0.1 to 1000 mg and preferably 1 to 500 mg per adult in terms of the weight of a compound of the formula (I), and suitably divided into several portions per day and administered.

In order to obtain a desired effect, the dose of a parenteral agent, which varies depending on the age, body weight and severity of a disease of a patient, is usually, for example, 0.1 to 1000 mg and preferably 1 to 500 mg per adult in terms of the weight of a compound of the formula (I), and suitably administered by intravenous injection, intravenous drip infusion, subcutaneous injection or intramuscular injection.

A compound represented by the formula (I) may be used in combination with an additional agent effective for SFTSV infection. These are separately administered during the process for treatment, or the agent is combined with the compound represented by the formula (I) in a single dosage form such as a tablet, an intravenous solution or a capsule. Examples of the additional agent include ribavirin and favipiravir.

EXAMPLES

Now, the present invention will be more specifically described below by way of Examples; however, the scope of the present invention is not limited to them.

Example 1

Separation of SFTSV from Culture of Cells Taken from Patient Specimen (Materials and Methods)

Patient 1: (female), onset: May 17, 2013 and serum sampling: May 24, 2013

Patient 2: (female), onset: Mar. 26, 2013 and serum sampling: Apr. 4, 2013

Each of the samples was inoculated in Vero cells (70 to 80% confluent), which were then incubated at 37° C. for 2 hours and washed. A fresh culture fluid was added and culture was carried out for three days.

The culture supernatant was collected. RNA was extracted by use of a QIAmp Viral RNA Mini Kit from the sample, or the supernatant was treated with Sidestep Lysis and Stabilization Buffer (Agilent).

The RNA extracted or the sample treated was subjected to amplification by an RT-PCR method using a SFTSV specific primer(s). The amplified product to be desired was confirmed by use of a microchip electrophoresis apparatus (Bio Analyzer).

The cells were fixed with paraformaldehyde/methanol and then immunostained with SFTSV specific immune serum. In this manner, infected cells were identified.

(Results)

The results of electrophoresis are shown in FIG. 1.

Figure 2:
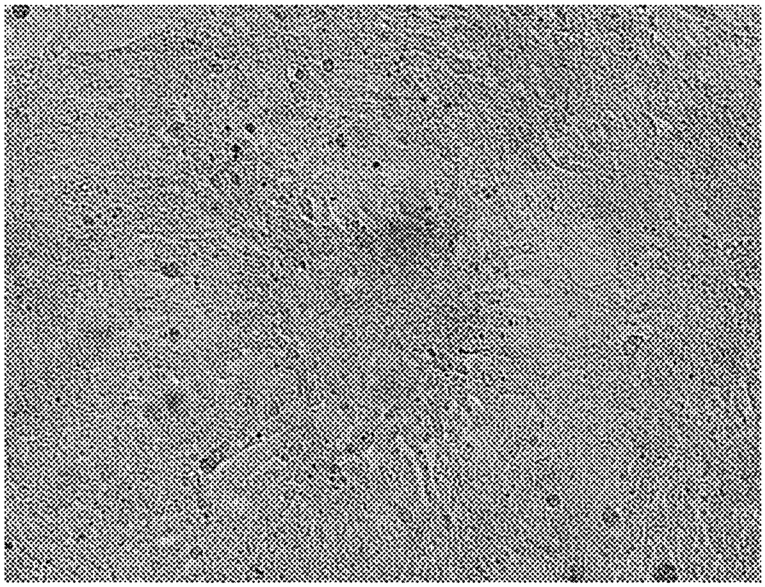
FIG. 2 is a photomicrograph of Vero cells (Day 3 after infection) infected with SFTSV.
Figure 3:
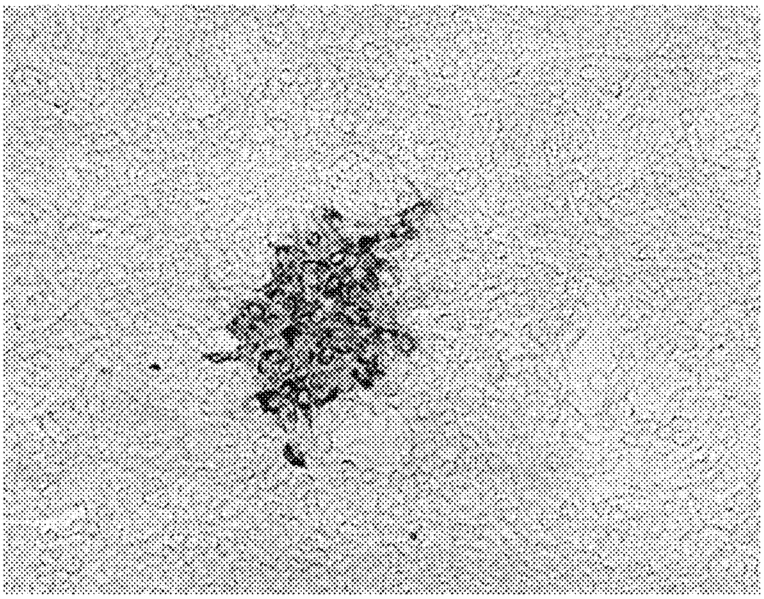
FIG. 3 is a photograph of immunostained Vero cells (Day 3 after infection) infected with SFTSV.

A photomicrograph of SFTSV infected Vero cells (Day 3 after infection) is shown in FIG. 2 and a photograph of the cells immunostained is shown in FIG. 3.

Example 2

Anti-SFTSV Effect (Virus)

SFTSV separated from a patient serum by use of Vero cells was subcultured by using HuH-7 cells derived from human hepatocytes. The culture supernatant thereof was used as a virus solution for assay. The infectivity titer of the virus was determined by immunohistochemical staining using Vero cells and counting the foci of infected cells.

(Method)

Vero cells were seeded on a microplate ($2\times10^4$ cells/well). After culture was carried out for 24 hours, various concentration of drugs and virus (MOI=0.01) were added. Culture was carried out at 37° C. for three days.

The anti-SFTSV effect of the drug was examined by washing the cells once with PBS, subjecting the cells to real time RT-PCR using a TaqMan Gene Expression Cells-to-CT™ Kit (Thermo Fisher Scientific Inc.) and determining the amount of viral RNA per well.

The cytotoxicity of a drug was examined by adding the various concentration of drugs to uninfected Vero cells and culturing the Vero cells for 3 days and counting the number of surviving cells by a dye method.

Since ribavirin and favipiravir are drugs already reported to have an anti-SFTSV effect (Tani H, et al., Efficacy of T-705 (favipiravir) in the treatment of infections with lethal severe fever with thrombocytopenia syndrome virus, mSphere 1 (1): e00061-15 (2016)), these were used as control drugs.

Figure 4:
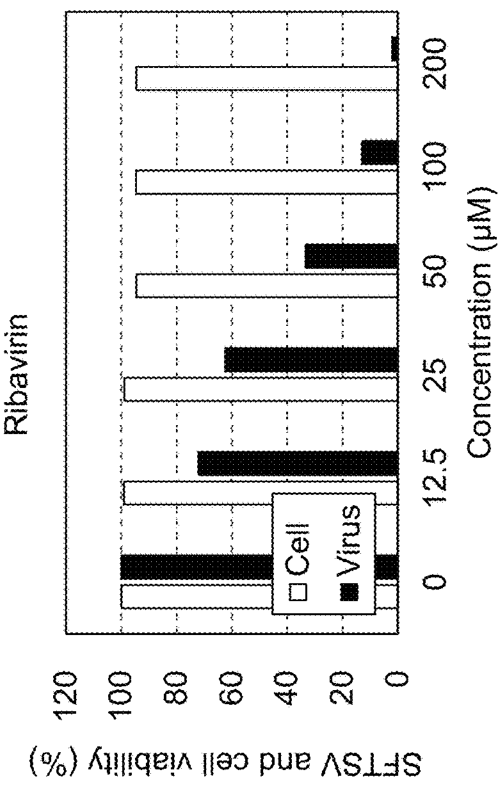
FIG. 4 shows the anti-SFTSV effect of amodiaquine, ribavirin and favipiravir.
Figure 4:
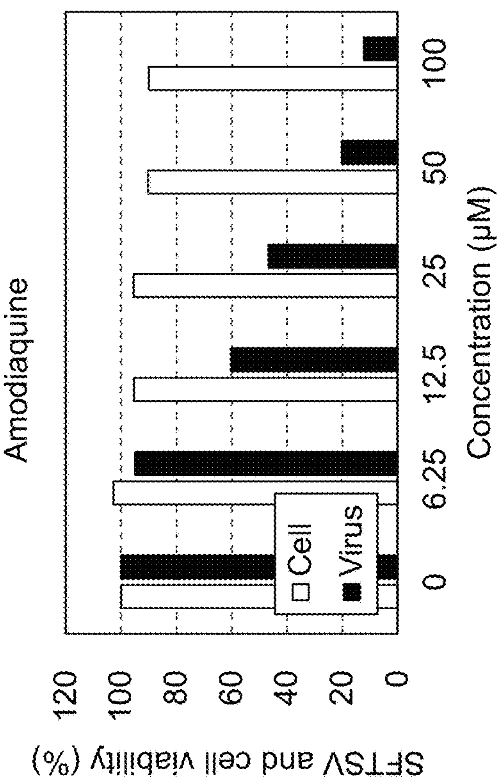
Figure 4:
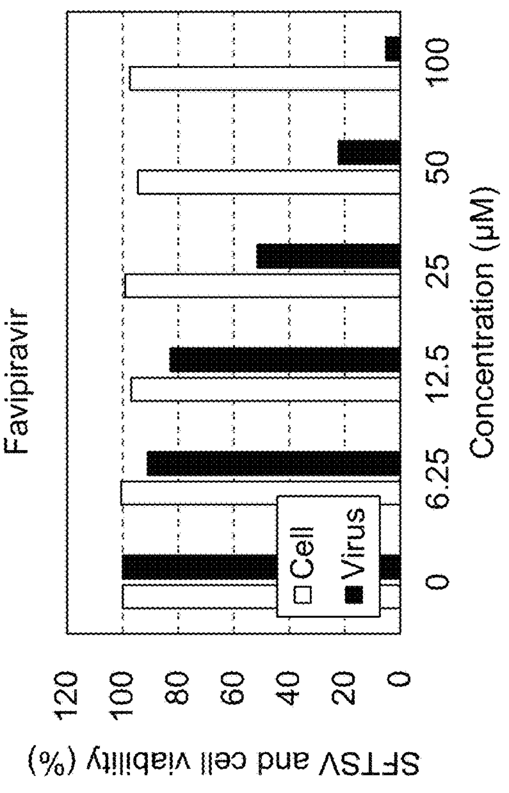

The results are shown in Table 1 and FIG. 4.

TABLE 1

| No. (name of drug) | Chemical structure | $EC_{50}$ (μM) | $CC_{50}$ (μM) |
|---|---|---|---|
| 1 (Amodiaquine) | 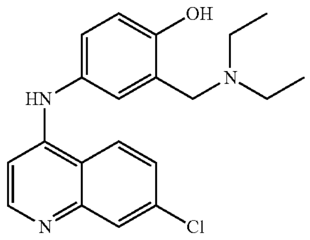 [SMILES: CCN(CC)Cc1cc(Nc2ccnc3cc(Cl)ccc23)ccc1O] | 19.1 ± 5.1 | >100 |
| 2 | 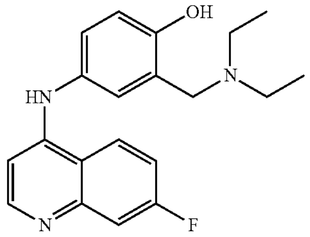 | 36.6 ± 9.3 | >100 |
| 3 | 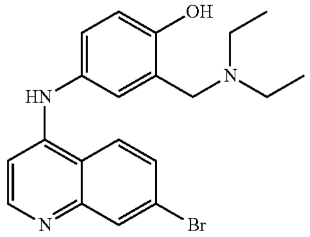 [SMILES: CCN(CC)Cc1cc(Nc2ccnc3cc(Br)ccc23)ccc1O] | 31.1 ± 16.8 | >100 |

TABLE 1-continued

| No. (name of drug) | Chemical structure | $EC_{50}$ (μM) | $CC_{50}$ (μM) |
| --- | --- | --- | --- |
| 4 | 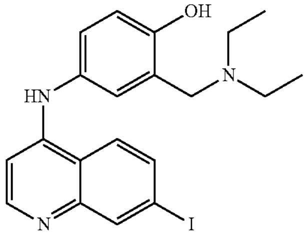 [SMILES: CCN(CC)Cc1cc(Nc2ccnc3cc(I)ccc23)ccc1O] | 15.6 ± 4.9 | >100 |
| 5 | 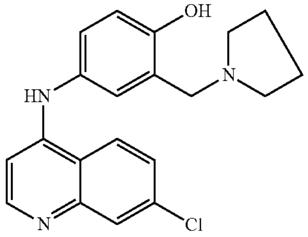 [SMILES: Oc1ccc(Nc2ccnc3cc(Cl)ccc23)cc1CN1CCCC1] | 14.6 | 41.1 |
| 6 | 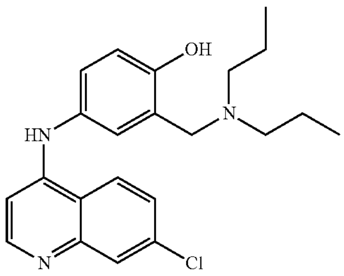 [SMILES: CCCN(CCC)Cc1cc(Nc2ccnc3cc(Cl)ccc23)ccc1O] | 58.7 | >100 |

$EC_{50}$: 50% effective concentration (concentration of a drug suppressing SFTSV proliferation by 50%)
$CC_{50}$: 50% cytotoxic concentration (concentration of a drug decreasing the number of surviving host cells by 50%)

Data of drugs 1 to 4 are mean values and SD values of three experiments; whereas, data of drugs 5 and 6 are single experimental results.

From Table 1 and FIG. 4, it is found that amodiaquine and its derivatives, and ribavirin and favipiravir have an anti-SFTSV effect.

Of the drugs, amodiaquine, ribavirin and favipiravir were commercially available products.

Amodiaquine derivatives were synthesized as follows.

Example 3

Synthesis of Compound 2: 4-(7-fluoroquinolin-4-ylamino)-2-diethylaminomethylphenol

[Formula 4]

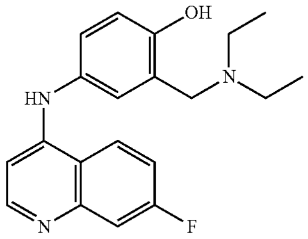

Scheme for synthesizing the title compound is shown below. In the scheme, "reflux" refers to a refluxing treatment.

[Formula 5]

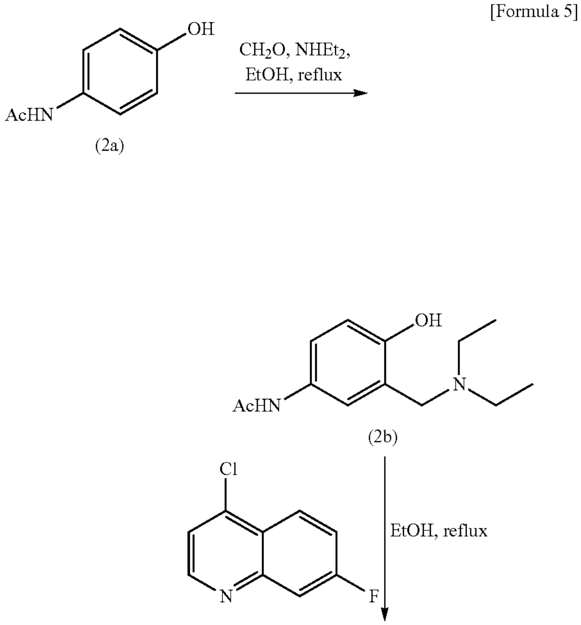

-continued

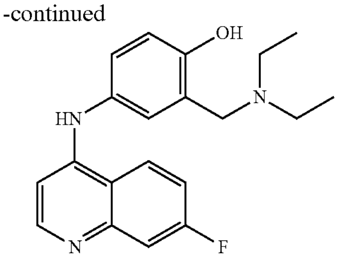

(2)

A mixture of 4-acetamidophenol (2a) (858.6 mg, 5.68 mmol) and 37% formaldehyde (848 μL, 8.52 mmol) was dissolved with ethanol (5 mL). Subsequently, diethylamine (881 μl, 8.52 mmol) was added and the mixture was refluxed for about 12 hours. The solvent was distilled off under reduced pressure and the resulting residue was isolated and purified by column chromatography (ethyl acetate:methanol=5:1) to obtain N-[3-{(diethylamino)methyl}-4-hydroxyphenyl]acetamide (2b) (871.2 mg, 3.69 mmol, yield 65%) as a white crystal. Then, a mixture of N-[3-{(diethylamino)methyl}-4-hydroxyphenyl]acetamide (2b) (133.6 mg, 0.50 mmol) and 4-chloro-7-fluoroquinoline (95.3 mg, 0.53 mmol) was dissolved with ethanol (5 mL) and refluxed for about 6 hours. The temperature of the reaction solution was controlled to be 0° C. While stirring, 2% ammonia water (about 5 mL) was added. The crystal was precipitated and separated by a Hirsch funnel. The resultant coarse crystal was recrystallized from methanol to obtain the title compound (2) (108.5 mg, 0.32 mmol, yield 64%) as a gray powder. The compound obtained was subjected to $^1H$ and $^{13}C$ NMR spectroscopies, high resolution mass spectroscopy (HRMS) and measurement of melting point (mp). The results are shown below.

$^1H$ NMR (400 MHz, $CDCl_3$): δ 8.45 (1H, d, J 5.6, quinoline-H), 7.89 (1H, m, quinoline-H), 7.63 (1H, m, quinoline-H), 7.25 (1H, m, quinoline-H), 7.09 (1H, dd, J 8.4 and 2.4, Ar—H), 6.93 (1H, d, J 2.4, Ar—H), 6.86 (1H, d, J 8.4, Ar—H), 6.60 (1H, brs, Ar—OH), 6.59 (1H, d, J 5.6, quinoline-H), 3.78 (2H, s, $ArCH_2N$), 2.65 (4H, q, J 7.2, $NCH_2CH_3$), 1.14 (6H, t, J 7.2, $NCH_2CH_3$); $^{13}C$ NMR (100 MHz, $CDCl_3$): δ 163.1 (d, J 248), 156.7, 151.9, 150.1 (d, J 12), 149.6, 129.9, 125.6, 125.3, 123.3, 121.7 (d, J 10), 117.2, 115.9, 115.0 (d, J 25), 113.4 (d, J 20), 100.8, 56.8, 50.8, 46.5, 11.2; HRMS (ESI) Calcd for $C_{20}H_{23}FN_3O^+[M+H]^+$: 340.18197. Found 340.18174; mp: 185.5-186.7° C.

Example 4

Synthesis of Compound 3: 4-(7-bromoquinolin-4-ylamino)-2-diethylaminomethylphenol

[Formula 6]

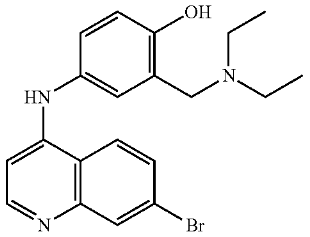

Synthesis was performed in the same procedure as in Example 3 except that 4-chloro-7-fluoroquinoline (95.3 mg, 0.53 mmol) was replaced by 4-chloro-7-bromoquinoline (126.5 mg, 0.53 mmol) to obtain the title compound (144.2 mg, 0.36 mmol, yield 72%) as a brown powder. The compound obtained was subjected to $^1H$ and $^{13}C$ NMR spectroscopies, high resolution mass spectroscopy (HRMS) and measurement of melting point (mp). The results are shown below.

$^1H$ NMR (400 MHz, $CDCl_3$): δ 8.45 (1H, d, J 5.2, quinoline-H), 8.18 (1H, d, J 2.4, quinoline-H), 7.75 (1H, d, J 8.8, quinoline-H), 7.56 (1H, dd, J 8.8 and 2.4, quinoline-H), 7.08 (1H, dd, J 8.4 and 2.4, Ar—H), 6.92 (1H, d, J 2.4, Ar—H), 6.86 (1H, d, J 8.4, Ar—H), 6.64 (1H, d, J 5.2, quinoline-H), 6.57 (1H, brs, Ar—OH), 3.79 (2H, s, $ArCH_2N$), 2.66 (4H, q, J 7.2, $NCH_2CH_3$), 1.14 (6H, t, J 7.2, $NCH_2CH_3$); $^{13}C$ NMR (100 MHz, $CDCl_3$): δ 156.7, 151.8, 149.6, 149.5, 132.1, 129.9, 128.3, 125.6, 125.3, 123.4, 121.0, 117.7, 117.1, 101.4, 56.8, 50.9, 46.4, 11.2; HRMS (ESI) Calcd for $C_{20}H_{23}BrN_3O^+[M+H]^+$: 400.10190. Found 400.10155; mp: 194.3-195.8° C.

Example 5

Synthesis of Compound 4: 4-(7-iodoquinolin-4-ylamino)-2-diethylaminomethylphenol

[Formula 7]

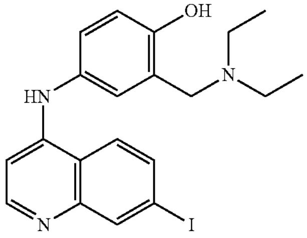

Synthesis was performed in the same procedure as in Example 3 except that 4-chloro-7-fluoroquinoline (95.3 mg, 0.53 mmol) was replaced by 4-chloro-7-iodoquinoline (91.0 mg, 0.32 mmol) to obtain the title compound (125.2 mg, 0.28 mmol, yield 93%) as a gray powder. The compound obtained was subjected to $^1H$ and $^{13}C$ NMR spectroscopies, high resolution mass spectroscopy (HRMS) and measurement of melting point (mp). The results are shown below.

$^1H$ NMR (400 MHz, $CDCl_3$): δ 8.44 (1H, d, J 5.2, quinoline-H), 8.42 (1H, d, J 1.2, quinoline-H), 7.72 (1H, dd, J 8.8 and 1.2, quinoline-H), 7.60 (1H, d, J 8.8, quinoline-H), 7.08 (1H, dd, J 8.4 and 2.4, Ar—H), 6.92 (1H, d, J 2.4, Ar—H), 6.86 (1H, d, J 8.4, Ar—H), 6.64 (1H, d, J 5.2, quinoline-H), 6.55 (1H, brs, Ar—OH), 3.78 (2H, s, $ArCH_2N$), 2.65 (4H, q, J 7.2, $NCH_2CH_3$), 1.14 (6H, t, J 7.2, $NCH_2CH_3$); $^{13}C$ NMR (100 MHz, $CDCl_3$): δ 156.7, 151.5, 149.8, 149.4, 138.8, 133.5, 129.8, 125.5, 125.3, 123.4, 120.8, 118.1, 117.2, 101.5, 95.3, 56.8, 46.4, 11.2; HRMS (ESI) Calcd for $C_{20}H_{23}IN_3O^+[M+H]^+$: 448.08803. Found 448.08638; mp: 189.7-190.4° C.

Example 6

Synthesis of Compound 5: 4-(7-chloroquinolin-4-ylamino)-2-(1-pyrrolidinylmethyl)phenol

[Formula 8]

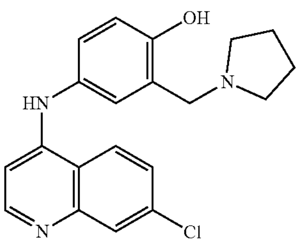

Synthesis was performed in the same procedure as in Example 3 except that diethylamine (881 μl, 8.52 mmol) was replaced by pyrrolidine (705 μl, 8.52 mmol) and that 4-chloro-7-fluoroquinoline (95.3 mg, 0.53 mmol) was replaced by 4,7-dichloroquinoline (614.4 mg, 3.10 mmol) to obtain the title compound (402.8 mg, 1.13 mmol, yield 40%) as a brown solid. The compound obtained was subjected to $^1H$ and $^{13}C$ NMR spectroscopies, high resolution mass spectroscopy (HRMS) and measurement of melting point (mp). The results are shown below.

$^1H$ NMR (400 MHz, $CDCl_3$): δ 8.45 (1H, d, J 5.2, quinoline-H), 8.00 (1H, d, J 2.0, quinoline-H), 7.86 (1H, d, J 8.4, quinoline-H), 7.42 (1H, dd, J 8.4 and 2.0, quinoline-H), 7.10 (1H, dd, J 8.4 and 2.4, Ar—H), 6.95 (1H, d, J 2.4, Ar—H), 6.87 (1H, d, J 8.4, Ar—H), 6.71 (1H, brs, Ar—OH), 6.63 (1H, d, J 5.2, quinoline-H), 3.84 (2H, s, $ArCH_2N$), 2.68 (4H, m, pyrrolidinyl-H), 1.88 (4H, m, pyrrolidinyl-H); $^{13}C$ NMR (100 MHz, $CDCl_3$): δ 156.5, 151.5, 149.5, 149.1, 135.3, 129.7, 128.6, 125.8, 125.6, 124.8, 123.7, 121.1, 117.3, 117.1, 101.3, 58.6, 53.6, 23.7; HRMS (ESI) Calcd for $C_{20}H_{21}ClN_3O^+[M+H]^+$: 354.13677. Found 354.13608; mp: 188.8-190.0° C.

Example 7

Synthesis of compound 6: 4-(7-chloroquinolin-4-ylamino)-2-dipropylaminomethylphenol

[Formula 9]

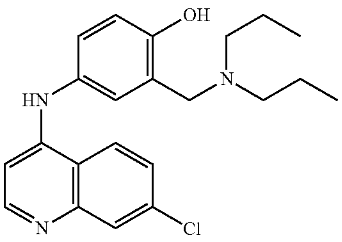

Synthesis was performed in the same procedure as in Example 3 except that diethylamine (881 μl, 8.52 mmol) was replaced by dipropylamine (1168 μl, 8.52 mmol) and that 4-chloro-7-fluoroquinoline (95.3 mg, 0.53 mmol) was replaced by 4,7-dichloroquinoline (614.4 mg, 3.10 mmol) to obtain the title compound (529.8 mg, 1.38 mmol, yield 46%) as a pale yellow solid. The compound obtained was subjected to $^1H$ and $^{13}C$ NMR spectroscopies, high resolution mass spectroscopy (HRMS) and measurement of melting point (mp). The results are shown below.

$^1H$ NMR (400 MHz, $CDCl_3$): δ 8.48 (1H, d, J 5.2, quinoline-H), 8.00 (1H, d, J 2.4, quinoline-H), 7.82 (1H, d, J 8.8, quinoline-H), 7.42 (1H, dd, J 8.8 and 2.4, quinoline-H), 7.09 (1H, dd, J 8.4 and 2.0, Ar—H), 6.92 (1H, d, J 2.4, Ar—H), 6.86 (1H, d, J 8.4, Ar—H), 6.63 (1H, d, J 5.2, quinoline-H), 6.57 (1H, brs, Ar—OH), 3.77 (2H, s, $ArCH_2N$), 2.51 (4H, m, $NCH_2CH_2CH_3$), 1.56 (4H, m, $NCH_2CH_2CH_3$), 0.92 (6H, t, J 7.2, $NCH_2CH_2CH_3$); $^{13}C$ NMR (100 MHz, $CDCl_3$): δ 156.6, 152.0, 149.6, 149.3, 135.1, 129.9, 129.0, 125.7, 125.5, 125.3, 123.5, 121.0, 117.4, 117.1, 101.4, 58.1, 55.5, 19.5, 11.8; HRMS (ESI) Calcd for $C_{22}H_{27}ClN_3O^+[M+H]^+$: 384.18372. Found 384.18302; mp: 163.2-164.3° C.

Example 8

Synthesis of Various Amodiaquine Derivatives

The following amodiaquine derivatives were obtained using the same procedure as in Examples 3-7.

Compound 7: 4-(7-iodoquinolin-4-ylamino)-2-dimethylaminomethylphenol

Compound 8: 4-(7-iodoquinolin-4-ylamino)-2-ethylmethylaminomethylphenol

Compound 9: 4-(7-iodoquinolin-4-ylamino)-2-isopropylmethylaminomethylphenol

Compound 10: 4-(7-iodoquinolin-4-ylamino)-2-tert-butylmethylaminomethylphenol

Compound 11: 4-(7-iodoquinolin-4-ylamino)-2-methylpropylaminomethylphenol

Compound 12: 4-(7-iodoquinolin-4-ylamino)-2-butylmethylaminomethylphenol

Compound 13: 4-(7-iodoquinolin-4-ylamino)-2-methylpentylaminomethylphenol

Compound 14: 4-(7-iodoquinolin-4-ylamino)-2-hexylmethylaminomethylphenol

Compound 15: 4-(7-iodoquinolin-4-ylamino)-2-methyloctylaminomethylphenol

Compound 16: 4-(7-iodoquinolin-4-ylamino)-2-ethyl(2-hydroxyethyl)aminomethylphenol Compound 17: 4-(7-iodoquinolin-4-ylamino)-2-ethylpropylaminomethylphenol Compound 18: 4-(7-iodoquinolin-4-ylamino)-2-ethylbutylaminomethylphenol Compound 19: 4-(7-iodoquinolin-4-ylamino)-2-(1-pyrrolidinylmethyl)phenol Compound 20: 4-(7-iodoquinolin-4-ylamino)-2-(1-piperidinylmethyl)phenol Compound 21: 4-(7-iodoquinolin-4-ylamino)-2-(4-morpholinylmethyl)phenol Compound 22: 4-(7-iodoquinolin-4-ylamino)-2-(4-thiamorpholinylmethyl)phenol

[Formula 10]

7

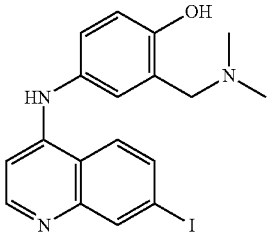

Chemical Formula: $C_{16}H_{18}IN_3O$
Molecular Weight: 419.25949

8

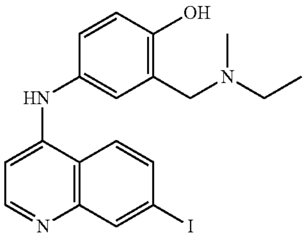

Chemical Formula: $C_{19}H_{20}IN_3O$
Molecular Weight: 433.28607

9

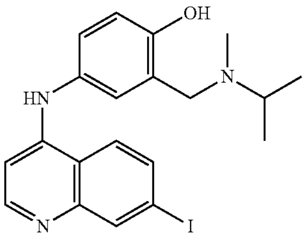

Chemical Formula: $C_{20}H_{22}IN_3O$
Molecular Weight: 447.31265

10

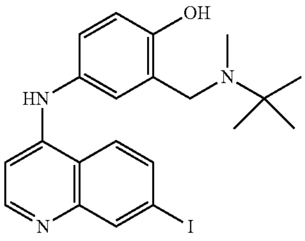

Chemical Formula: $C_{21}H_{24}IN_3O$
Molecular Weight: 461.33923

11

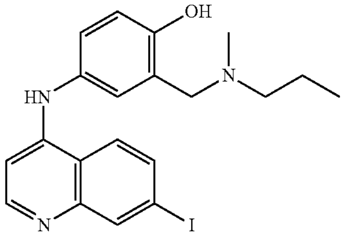

Chemical Formula: $C_{20}H_{22}IN_3O$
Molecular Weight: 447.31265

-continued

12

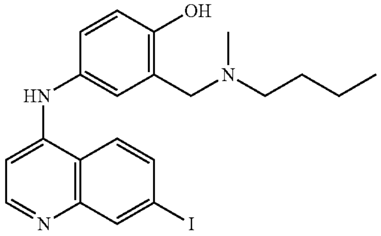

Chemical Formula: $C_{21}H_{24}IN_3O$
Molecular Weight: 461.33923

13

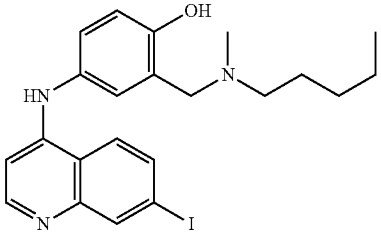

Chemical Formula: $C_{22}H_{26}IN_3O$
Molecular Weight: 475.36581

14

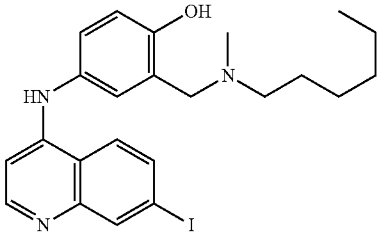

Chemical Formula: $C_{23}H_{28}IN_3O$
Molecular Weight: 489.39239

15

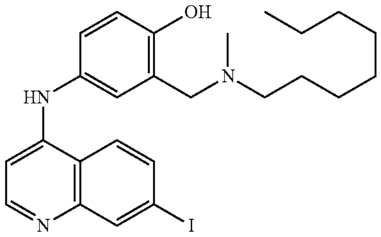

Chemical Formula: $C_{25}H_{32}IN_3O$
Molecular Weight: 517.44555

16

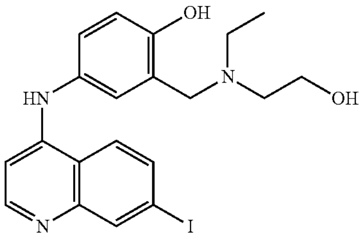

Chemical Formula: $C_{20}H_{22}IN_3O_2$
Molecular Weight: 463.31205

-continued

17

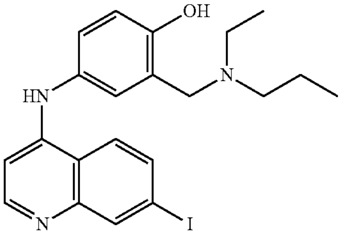

Chemical Formula: $C_{21}H_{24}IN_3O$
Molecular Weight: 461.33923

18

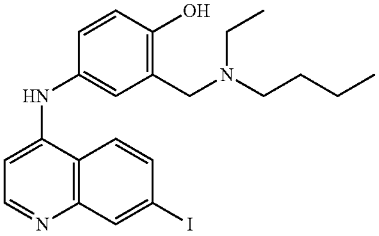

Chemical Formula: $C_{22}H_{25}IN_3O$
Molecular Weight: 475.36581

19

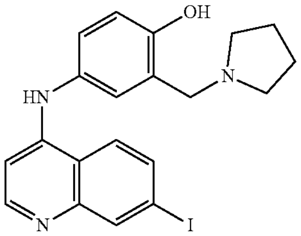

Chemical Formula: $C_{20}H_{20}IN_3O$
Molecular Weight: 445.29677

20

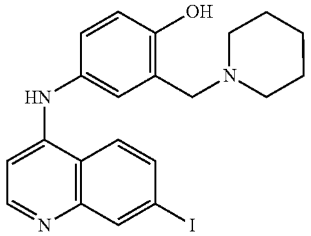

Chemical Formula: $C_{21}H_{22}IN_3O$
Molecular Weight: 459.32335

-continued

21

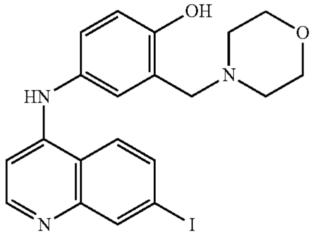

Chemical Formula: $C_{20}H_{20}IN_3O_2$
Molecular Weight: 461.29617

22

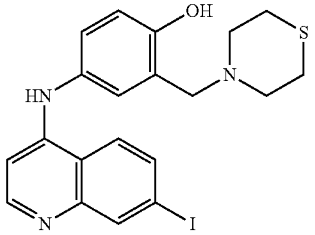

Chemical Formula: $C_{20}H_{20}IN_3OS$
Molecular Weight: 477.36177

Example 9

Anti-SFTSV Effect

The amodiaquine derivatives described in Example 8 were examined for anti-SFTSV effect and cytotoxicity in the same procedure as in Example 2.

Figure 5:
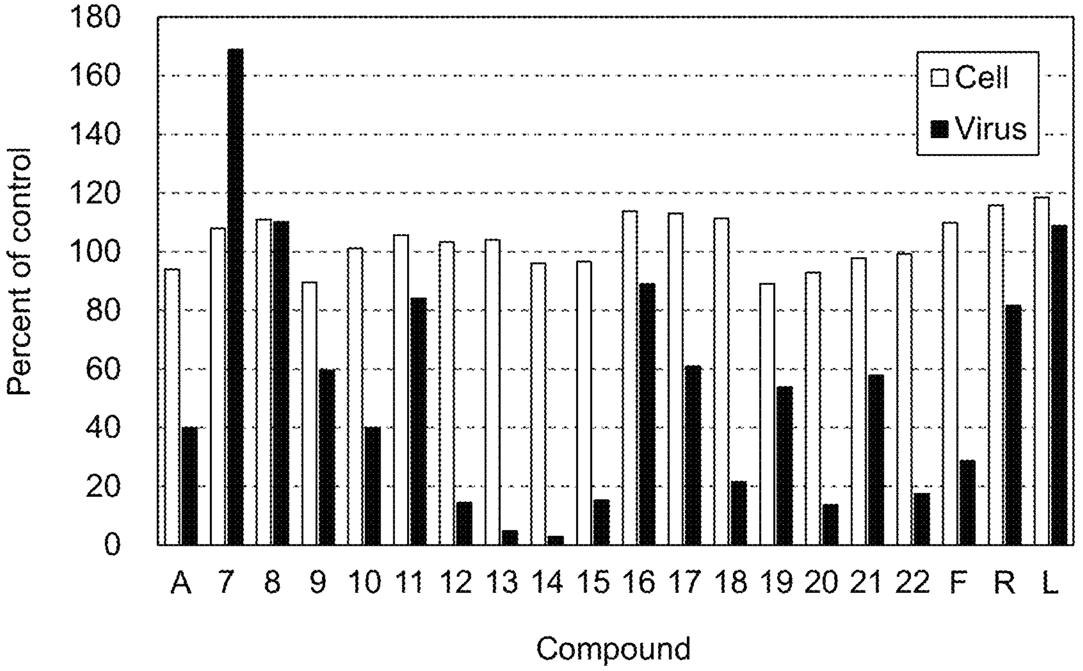
FIG. 5 shows the anti-SFTSV effect of amodiaquine, various amodiaquine derivatives, favipiravir, ribavirin and lamivudine.

A screening test was carried out by fixing the concentrations of the drugs all at 10 μM. The results are shown in FIG. 5. In FIG. 5, the "Percent of control" on the vertical axis represents percentage based on the proliferation (100%) of SFTSV in a case without drug addition.

The compounds of Nos. 12 to 14, which exhibited particularly excellent activity in the screening test, were examined for anti-SFTSV effect and cytotoxicity. The results are shown in Table 2.

TABLE 2

| | Chemical structure | $EC_{50}$ (μM) | $CC_{50}$ (μM) |
|---|---|---|---|
| Compound 12 | 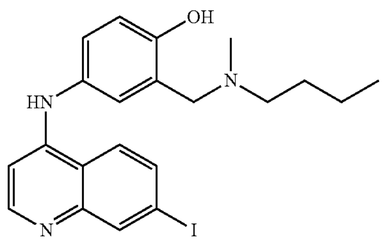 [SMILES: CCCCN(C)Cc1cc(Nc2ccnc3cc(I)ccc23)ccc1O] | 6.2 | >50 |

TABLE 2-continued

| | Chemical structure | $EC_{50}$ (μM) | $CC_{50}$ (μM) |
|---|---|---|---|
| Compound 13 | 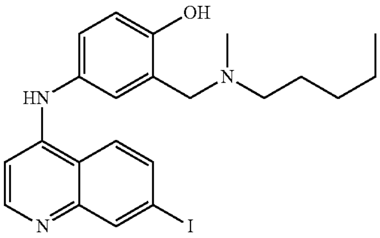 [SMILES: CCCCCN(C)Cc1cc(Nc2ccnc3cc(I)ccc23)ccc1O] | 3.4 | >50 |
| Compound 14 | 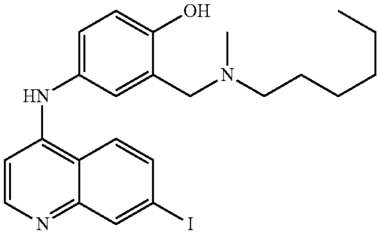 [SMILES: CCCCCCN(C)Cc1cc(Nc2ccnc3cc(I)ccc23)ccc1O] | 8.7 | >50 |

The invention claimed is:

1. A compound represented by the following formula (Ia):

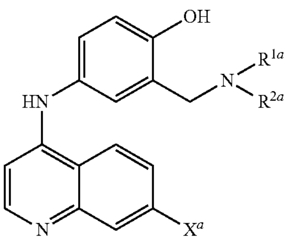

(Ia)

wherein $R^{1a}$ and $R^{2a}$ represent a combination of a methyl group and a $C_{4-10}$-alkyl group, or a combination of an ethyl group and a $C_{4-10}$-alkyl group, and may join with an adjacent nitrogen atom to form a 1-piperidinyl group or a 4-thiamorpholinyl group, both of which can be either substituted or unsubstituted; $X^a$ represents an iodine atom or a fluorine atom; if $X^a$ represents a fluorine atom, $R^{1a}$ and $R^{2a}$ may be an ethyl group and an ethyl group, or a salt thereof or a solvate thereof.

2. A method for treating or preventing severe fever with thrombocytopenia syndrome comprising administering to a subject in need thereof an effective amount of a compound represented by the following formula (I):

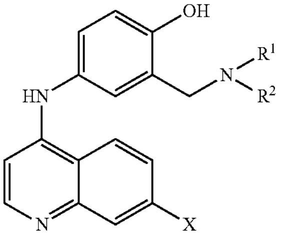

(I)

wherein $R^1$ and $R^2$, which are the same or different, each represent a substituted or unsubstituted $C_{1-10}$-alkyl group and may join with an adjacent nitrogen atom to form a substituted or unsubstituted 5-membered ring or 6-membered ring; and X represents a halogen atom, or a salt thereof or a solvate thereof.

3. The method of claim 2, wherein, in the formula (I), $R^1$ and $R^2$, which are the same or different, each represent a substituted or unsubstituted $C_{1-6}$-alkyl group and may join with an adjacent nitrogen atom to form a substituted or unsubstituted 5-membered ring or 6-membered ring; and X represents a halogen atom.

4. A method for treating or preventing severe fever with thrombocytopenia syndrome virus infection comprising administering to a subject in need thereof an effective amount of a compound represented by the following formula (I):

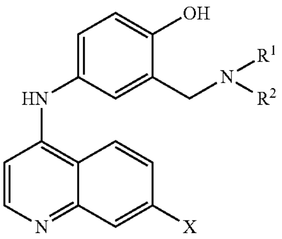

(I)

wherein $R^1$ and $R^2$, which are the same or different, each represent a substituted or unsubstituted $C_{1-10}$-alkyl group and may join with an adjacent nitrogen atom to form a substituted or unsubstituted 5-membered ring or 6-membered ring; and X represents a halogen atom, or a salt thereof or a solvate thereof.

5. The method of claim 4, wherein, in the formula (I), $R^1$ and $R^2$, which are the same or different, each represent a substituted or unsubstituted $C_{1-6}$-alkyl group and may join with an adjacent nitrogen atom to form a substituted or unsubstituted 5-membered ring or 6-membered ring; and X represents a halogen atom.

6. The compound of claim 1, wherein, in the formula (Ia), $X^a$ represents an iodine atom.

7. The compound of claim 1, which is selected from the group consisting of 4-(7-iodoquinolin-4-ylamino)-2-butylmethylaminomethylphenol, 4-(7-iodoquinolin-4-ylamino)-2-methylpentylaminomethylphenol, 4-(7-iodoquinolin-4-ylamino)-2-hexylmethylaminomethylphenol, 4-(7-iodoquinolin-4-ylamino)-2-methyloctylaminomethylphenol, 4-(7-iodoquinolin-4-ylamino)-2-ethylbutylaminomethylphenol, 4-(7-iodoquinolin-4-ylamino)-2-(1-piperidinylmethyl)phenol, and 4-(7-iodoquinolin-4-ylamino)-2-(4-thiamorpholinylmethyl)phenol.

8. The compound of claim 1, which is selected from the group consisting of 4-(7-iodoquinolin-4-ylamino)-2-butylmethylaminomethylphenol, 4-(7-iodoquinolin-4-ylamino)-2-methylpentylaminomethylphenol, and 4-(7-iodoquinolin-4-ylamino)-2-hexylmethylaminomethylphenol.

9. The compound of claim 1, wherein, in the formula (Ia), $R^{1a}$ and $R^{2a}$ join with an adjacent nitrogen atom to form a 1-piperidinyl group or a 4-thiamorpholinyl group, both of which can be either substituted or unsubstituted.

* * * * *